United States Patent
Quinn

(10) Patent No.: US 9,632,026 B2
(45) Date of Patent: Apr. 25, 2017

(54) OPTICAL BIOSENSOR REFERENCING METHOD

(71) Applicant: FLIR SYSTEMS, INC., Wilsonville, OR (US)

(72) Inventor: John Gerard Quinn, Edmond, OK (US)

(73) Assignee: FLIR Systems, Inc., Wilsonville, OR (US)

( * ) Notice: Subject to any disclaimer, the term of this patent is extended or adjusted under 35 U.S.C. 154(b) by 158 days.

(21) Appl. No.: 13/748,040

(22) Filed: Jan. 23, 2013

(65) Prior Publication Data

US 2013/0189797 A1   Jul. 25, 2013

Related U.S. Application Data

(60) Provisional application No. 61/589,731, filed on Jan. 23, 2012.

(51) Int. Cl.
| G01N 21/552 | (2014.01) |
| G01N 33/53  | (2006.01) |
| G01N 33/543 | (2006.01) |

(52) U.S. Cl.
CPC ........... *G01N 21/553* (2013.01); *G01N 33/53* (2013.01); *G01N 33/54373* (2013.01)

(58) Field of Classification Search
CPC .............................. G02B 5/008; G02B 6/1226
See application file for complete search history.

(56) References Cited

U.S. PATENT DOCUMENTS

| 5,858,799 A *  | 1/1999  | Yee et al. ................. 436/164 |
| 6,200,814 B1   | 3/2001  | Malmqvist et al. |
| 6,294,391 B1 * | 9/2001  | Badley et al. ............. 436/518 |
| 7,015,043 B2   | 3/2006  | Roos et al. |
| 7,105,356 B2   | 9/2006  | Malmqvist et al. |
| 7,309,614 B1 * | 12/2007 | Baird et al. .............. 436/518 |
| 7,582,487 B2   | 9/2009  | Malmqvist et al. |
| 7,736,587 B2   | 6/2010  | Malmqvist et al. |
| 8,021,626 B2   | 9/2011  | Malmqvist et al. |
| 8,298,496 B2   | 10/2012 | Quinn |
| 2004/0186359 A1 * | 9/2004  | Beaudoin et al. ......... 600/310 |
| 2004/0218184 A1 * | 11/2004 | Jorgenson et al. ........ 356/419 |
| 2006/0197954 A1 * | 9/2006  | Ogura et al. ............. 356/445 |
| 2008/0063569 A1 * | 3/2008  | Fontaine et al. ......... 422/82.11 |

FOREIGN PATENT DOCUMENTS

WO     WO 99/36766     7/1999

* cited by examiner

*Primary Examiner* — Rebecca Martinez
(74) *Attorney, Agent, or Firm* — McAfee & Taft, PC

(57) ABSTRACT

A referencing method for an optical biosensor system using a single sensing region is provided. The method involves limiting the ligand immobilized in a single sensing region to only a portion thereof. In one embodiment, this is accomplished by selectively deactivating a portion of the sensing surface to prevent immobilization of ligand to that portion. As a result, a reference response can be recorded in the same sensing region as a molecular interaction response. Thus, the bulk refractive index can be accurately accounted for in measuring the kinetics of a molecular interaction.

6 Claims, 9 Drawing Sheets

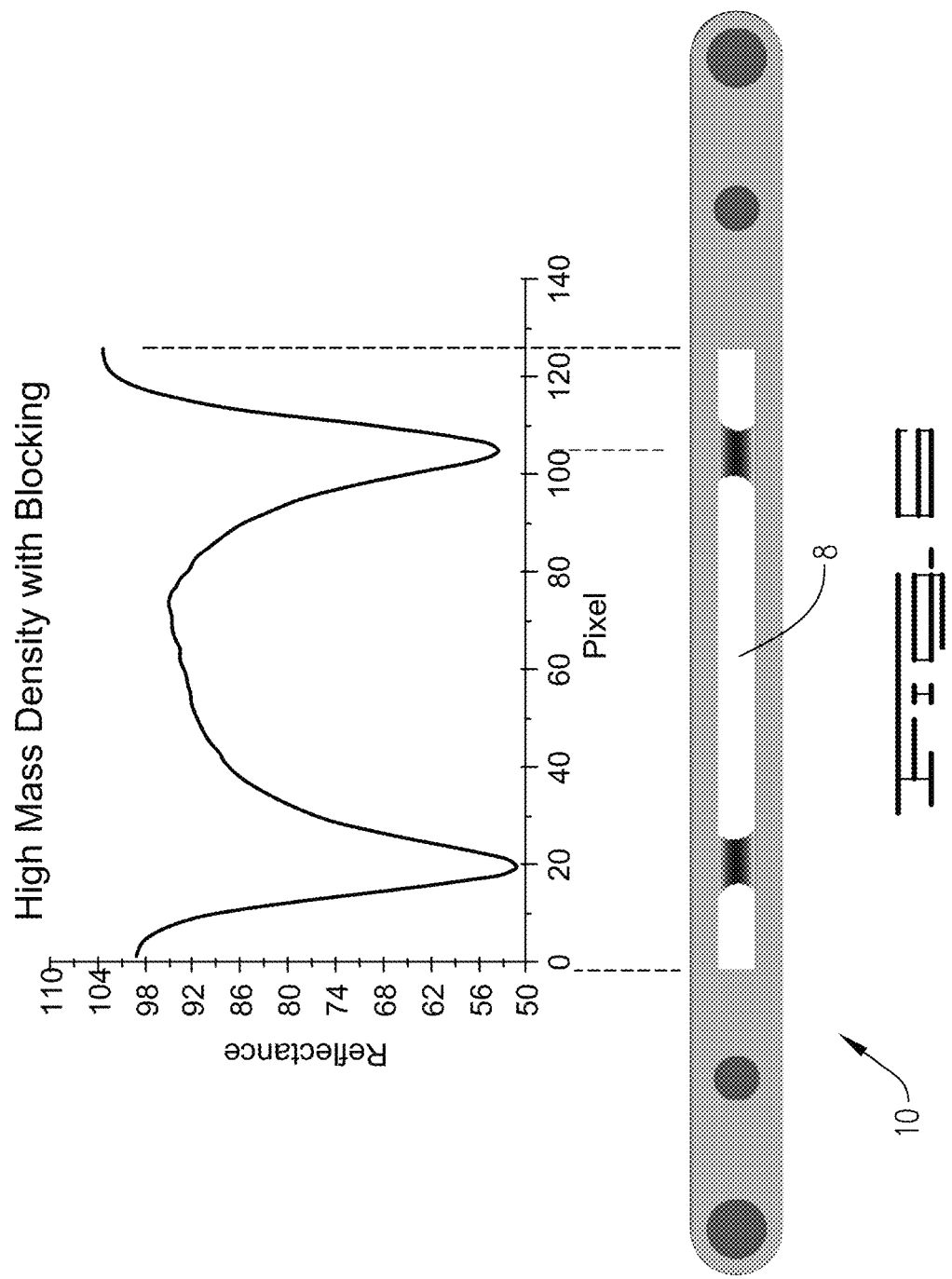

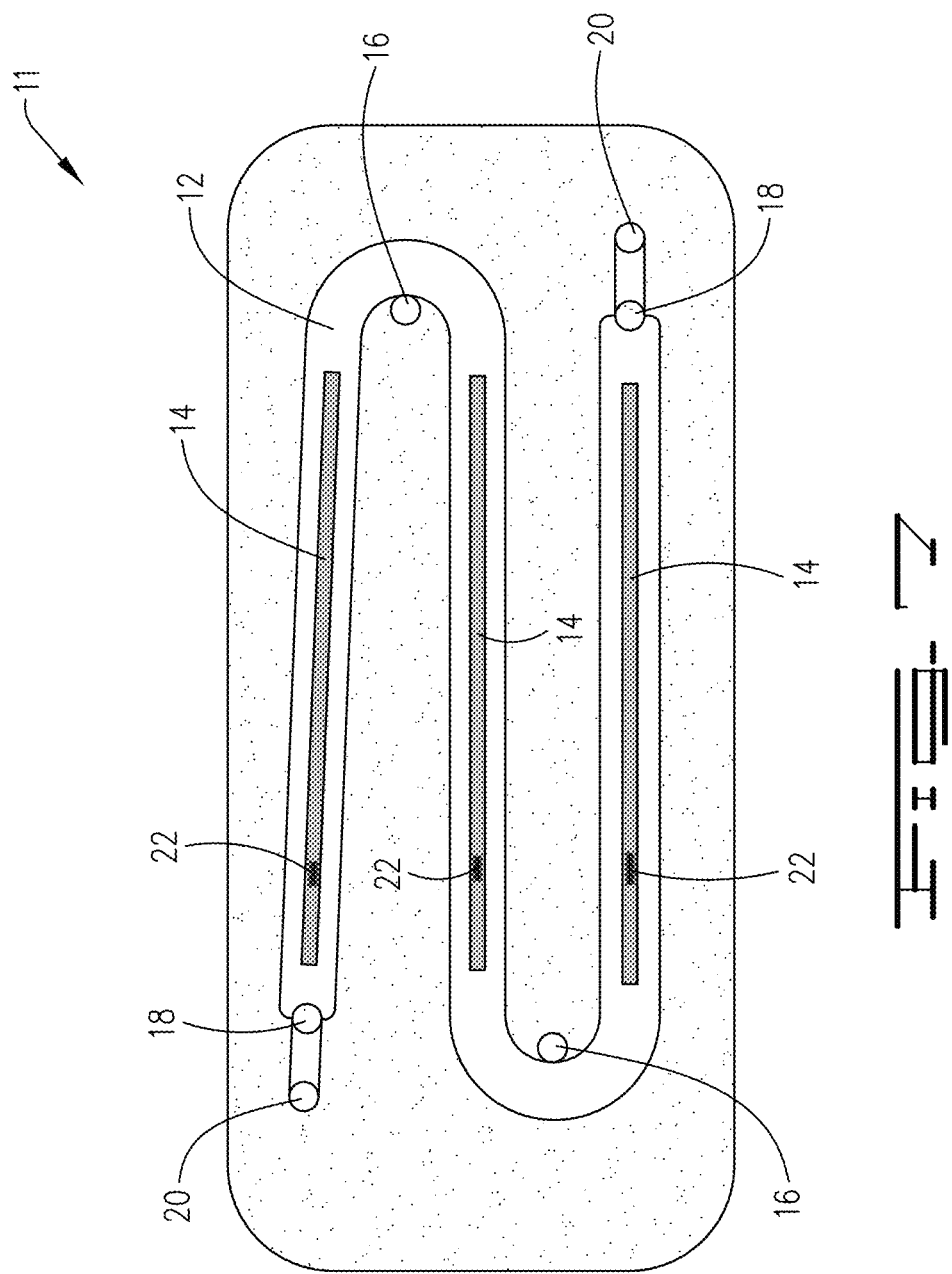

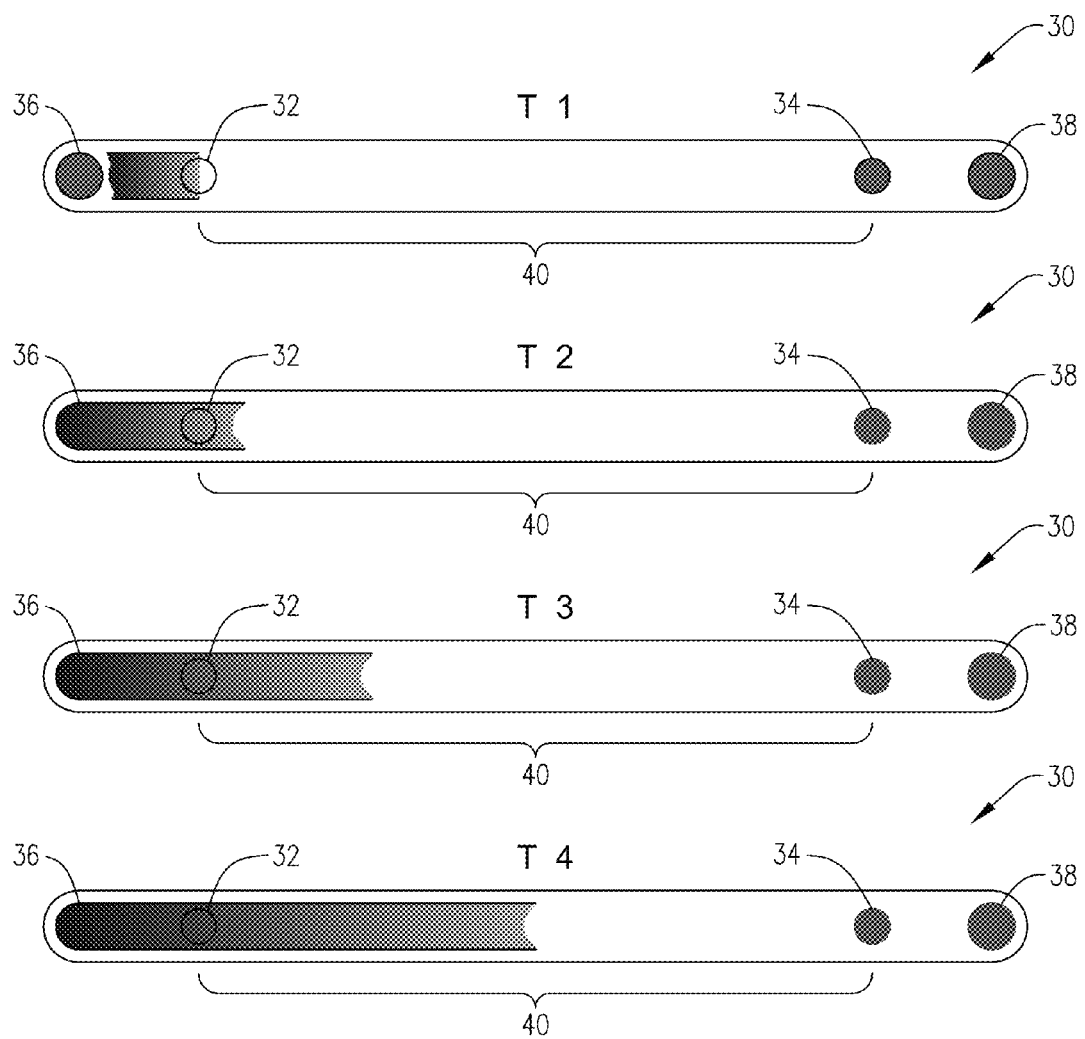

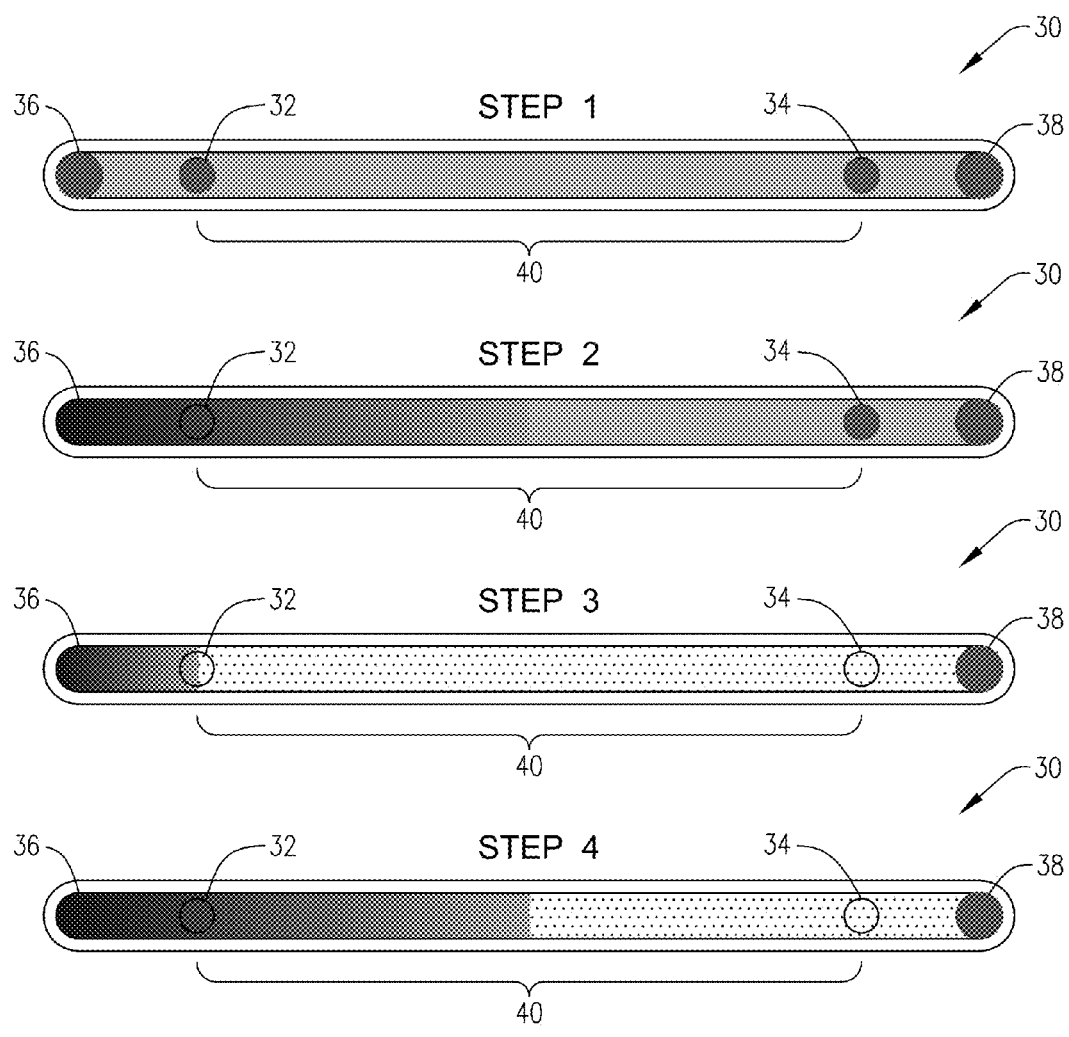

OPTICAL BIOSENSOR REFERENCING METHOD

CROSS-REFERENCE TO RELATED APPLICATIONS

The present application claims priority to U.S. Provisional Application No. 61/589,731 filed on Jan. 23, 2012.

BACKGROUND

Surface plasmon resonance (SPR) based biosensors are commonly used to perform kinetic studies of complex molecular interactions such as between hormone-receptor, enzyme-substrate and antigen-antibody. The biosensors are typically in the form of one or more sensing regions housed within a flow cell of a microfluidic system. The microfluidic system defines a series of flow paths that direct fluid flow to the flow cell containing the sensing regions. The one or more sensing regions of the flow cell support immobilized molecules referred to as "ligands." The ligands bind molecules known as "analytes" which are present in fluids that are directed to the sensing region via the microfluidic system. Current analysis methods determine the kinetic interaction of the ligand and analyte by separately injecting a series of analyte concentrations into the system and measuring the change in refractive index at the sensing regions. Based on the changes in refractive index, one can determine the real-time kinetics of the interaction between the analyte and ligand, including association and dissociation rates.

When the analyte being tested consists of a small molecule, the change in refractive index at the sensing region due to interaction with ligand is typically very small and may be difficult to detect above the refractive index from the bulk flow of the sample in the sensing region (bulk refractive index). This is typically a result of high concentrations of the small molecule or more commonly, high concentrations of solubilizing agent such as dimethylsulfoxide (DMSO). As such, a referencing method is needed that allows the response from the bulk refractive index to be separated from the response due to the molecular interaction between analyte and immobilized ligand at the sensing region.

The double referencing method has been one approach to solving this problem. In this method, the sample is caused to flow over two separate sensing regions; one of the sensing region contains immobilized ligand (working sensing region) and one sensing region is free of immobilized ligand (reference sensing region). Thus, the response from the reference sensing region can be subtracted from the response in the working sensing region to yield the response attributed to the molecular interaction in the working sensing region.

However, there are some limitations associated with this particular method. Differences, such as temperature, sensitivity and dispersion, between the working sensing region and reference sensing region can significantly impact the data quality and obscure the binding response, especially with low molecular weight molecules. Dispersion of the sample that may occur between the two sensing regions is of a particular concern. In most microfluidic systems, a buffer fluid will typically flow through the channels housing the sensing regions prior to exposure to the fluid containing the analyte sample. Since the sensing regions are separated, the sample is likely to encounter additional residual buffer in the flow path from the reference sensing region to the working sensing region. This causes dilution of the sample thereby changing the refractive index such that the response obtained from the reference sensing region is not entirely an accurate representation of the sample that encounters the working sensing region. These concerns are particularly pertinent when the bulk refractive index of the sample and buffer differ, even where the difference is small (e.g. 500 RU). These small differences can have profound effects on the accuracy of the kinetic calculations for the association and dissociation rates of the binding interactions between analyte and ligand. Thus, a method is needed that provides a reference measurement without the deleterious effects of a two sensing region referencing system.

SUMMARY

A method is provided that allows a single sensing region to be divided into two or more sub-regions, wherein one sub-region provides a reference measurement and one sub-region provides an interaction measurement thereby alleviating many of the problems associated with a separate reference sensing region. The method comprises the steps of activating an entire sensing region to permit immobilization of a ligand thereon, selectively deactivating a portion of the sensing region to prevent immobilization of a ligand as to the sub-region, and injecting the ligand over the sensing region to permit immobilization onto the portion of the activated portion of the sensing region. Thus, the method provides a single sensing region that has been divided into two portions, wherein a first portion provides a reference measurement (the portion that has been deactivated) and a second portion provides an interaction measurement (the activated portion containing the ligand). Specifically, the first portion encompasses an area of the sensing region that is interrogated by low surface plasmon resonance angles and the second portion encompasses an area of the sensing region that is interrogated by high surface plasmon resonance angles. Since the reference portion is in the same sensing region with the working portion, the concerns with dispersion and differences between separate sensing regions are eliminated, or at the least, minimized, thereby providing a more accurate referencing method. Additionally, the present method increases the data capability of a biosensor system since each sensing region in a microfluidic flow cell can be modified to include its own integrated reference point alleviating the need to use an entire separate sensing region for a reference point thereby increasing assay capacity with minimal added complexity.

In one embodiment, a method for providing a reference bulk refractive index response and a binding response in a single sensing region disposed along a channel in a flow cell of a biosensor system is provided. In the present embodiment, a first sample is injected through a first input port at a first end of a sensing region. The first sample comprises an activating agent sufficient to permit immobilization of a ligand onto the surface of the sensing region. The first sample flows from the first end of the sensing region to a second region where it exits via a second exit port. Once the surface of the sensing region has been sufficiently exposed to the sensing region, the injection of the first sample is terminated. A second sample is then injected at a flow rate through the first input port, wherein a first exit port located on the first end of the sensing region is opened and the second exit port is closed. The flow rate of the second sample is then modified in a manner sufficient to cause the second sample to contact only a first portion of the sensing region thereby defining a second portion of the sensing region that is not contacted by the second sample, wherein the second sample comprises a deactivating agent sufficient to render the first portion incapable of having ligand immobilized thereon. The extent of the migration of the second sample along the sensing region is selected to position the first portion in an area of the sensing region that is interrogated by low surface plasmon resonance angles such that the second portion encompasses an area of the sensing region that is interrogated by high surface plasmon resonance angles. Following termination of the second sample injection, a third sample comprising the ligand is injected through the first input port with the second exit port open and the first exit port closed such that first and second portions of the sensing region are exposed to the third sample. However, due to deactivation of the first portion, the ligand is only immobilized to the second portion of the sensing region. The third sample injection is terminated and thereafter, the analyte sample is injected through the first input port and caused to flow over the first and second portions of the sensing region. The responses at the first and second portions of the sensing region are recorded wherein the response at the first portion provides a reference response comprising the bulk refractive index and the response at the second portion includes the binding response resulting from the interaction between analyte and ligand. The reference response is then subtracted from response at the second portion to isolate the response elicited from the binding interaction.

BRIEF DESCRIPTION OF THE DRAWINGS

FIG. 6 depicts and exemplary high mass SPR dip and low mass SPR dip mapped to different sub-regions of a sensing region in accordance with the methods of the present invention.

FIG. 7 depicts a flow cell with a serpentine channel having three separate sensing regions disposed thereon.

FIG. 8 depicts a sub-addressing method used with the methods of the present invention.

FIG. 9 provides an illustration of one embodiment of the inventive method.

DETAILED DESCRIPTION

The ability to measure binding of small drug molecules to immobilized proteins in real time has become feasible mainly as a result of improved signal referencing methods such as the double referencing method. However, this method has some limitations related to how similar the reference sensing region is with respect to the working sensing region. Differences in temperature, sensitivity and dispersion at each location can have a significant impact on the data quality and can obscure the binding response expected from low molecular weight molecules. These concerns are extremely pertinent when the bulk refractive index of the sample and the continuous flow buffer differ by even a small amount (e.g. 500 RU). A particularly difficult issue is dispersion. This is where the dead volume that exists between the working sensing region and the referencing sensing region is sufficient to cause dilution of the sample and hence cause changes in the bulk refractive index injection profile that then translates into distortions of the double referenced data.

Figure 1:
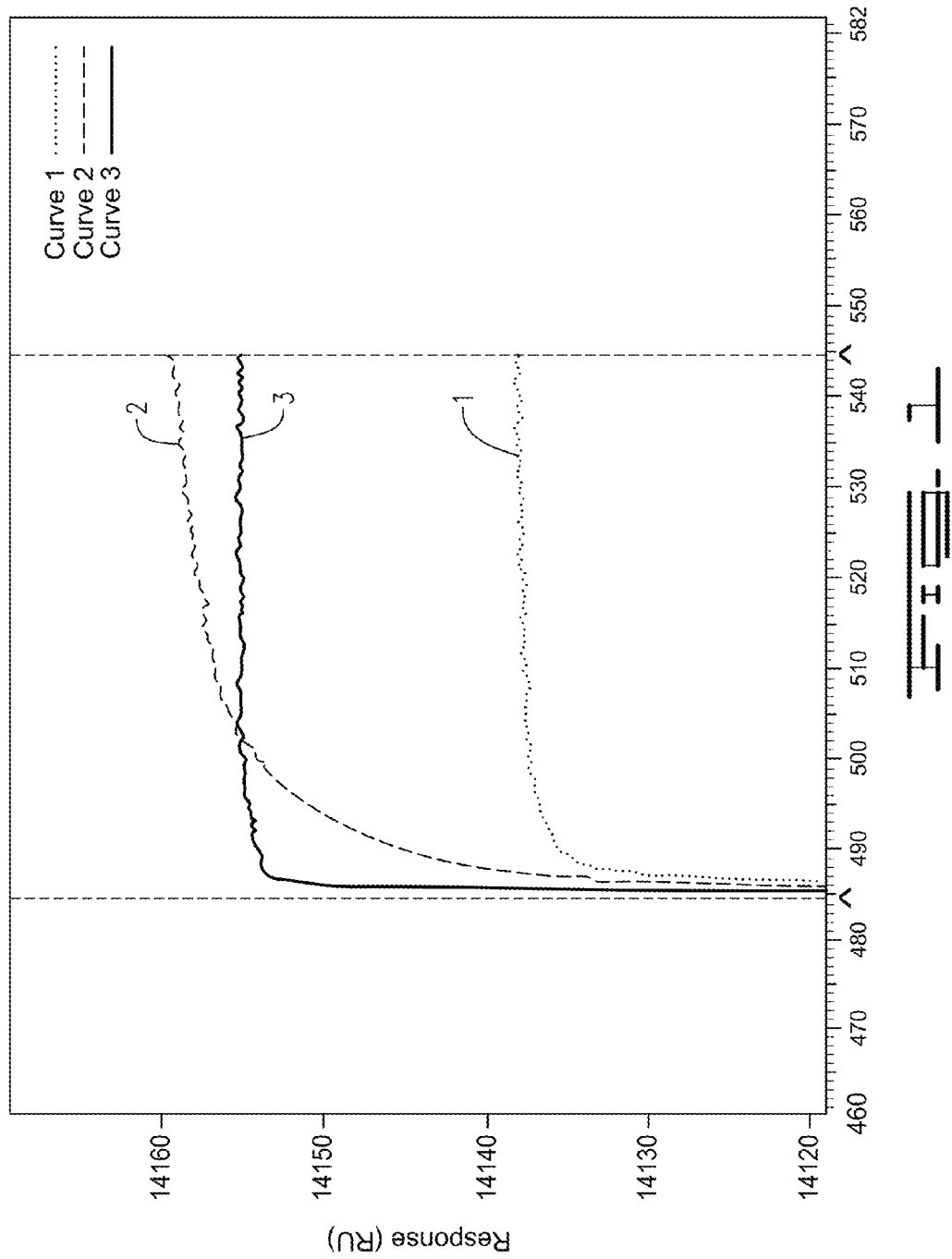
FIG. 1 depicts and injection profile of three independent sensing regions represented by curves 1, 2, and 3. Curves 1 and 3 represent injection profiles at sensing regions that were independently addressed whereas curve 2 represents an injection profile at a sensing region following exposure to a separate sensing region.

FIG. 1 shows a zoom view of an injection profile focusing on the plateau that forms during the injection (i.e. shaded region). As depicted therein, the second sensing region (curve 2) possesses far more curvature than the other two sensing regions. This curvature only represents 2% of the total bulk refractive index response, but has a serious negative impact on data quality when performing a kinetic analysis. The curvature in the second sensing region is caused by mixing with the running buffer that is present at an exit port located between the sensing regions.

Figure 2:
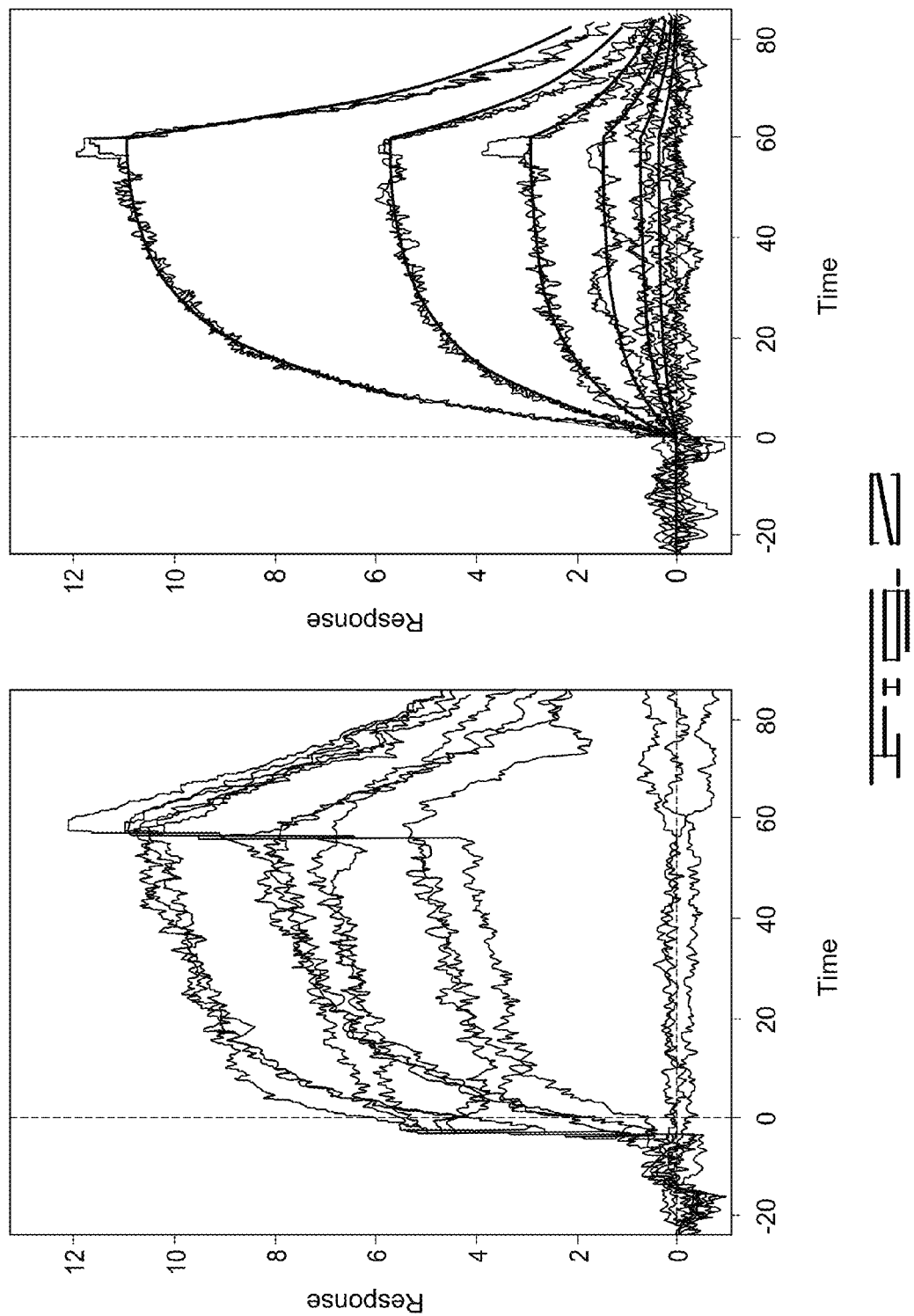
FIG. 2 depicts a set of exemplary responses elicited by a serial dilution. The curves in the right panel represent the bulk refractive index recorded at a reference sensing region and demonstrate the dispersion effect. The curves in the left panel represent the analyte binding curves at a separate working sensing region.

The effect of this curvature in the injection profile appears in the double referenced response as an apparent binding signal as shown in FIG. 2. The curves in the right panel show the dispersion effect isolated for a series of dilutions. The curves in the left panel represent the analyte binding curves that are distorted by the dispersion. If the dispersion effect is subtracted, the data set quality is improved to enable a reasonable kinetic model fit as shown in FIG. 3.

Figure 3:
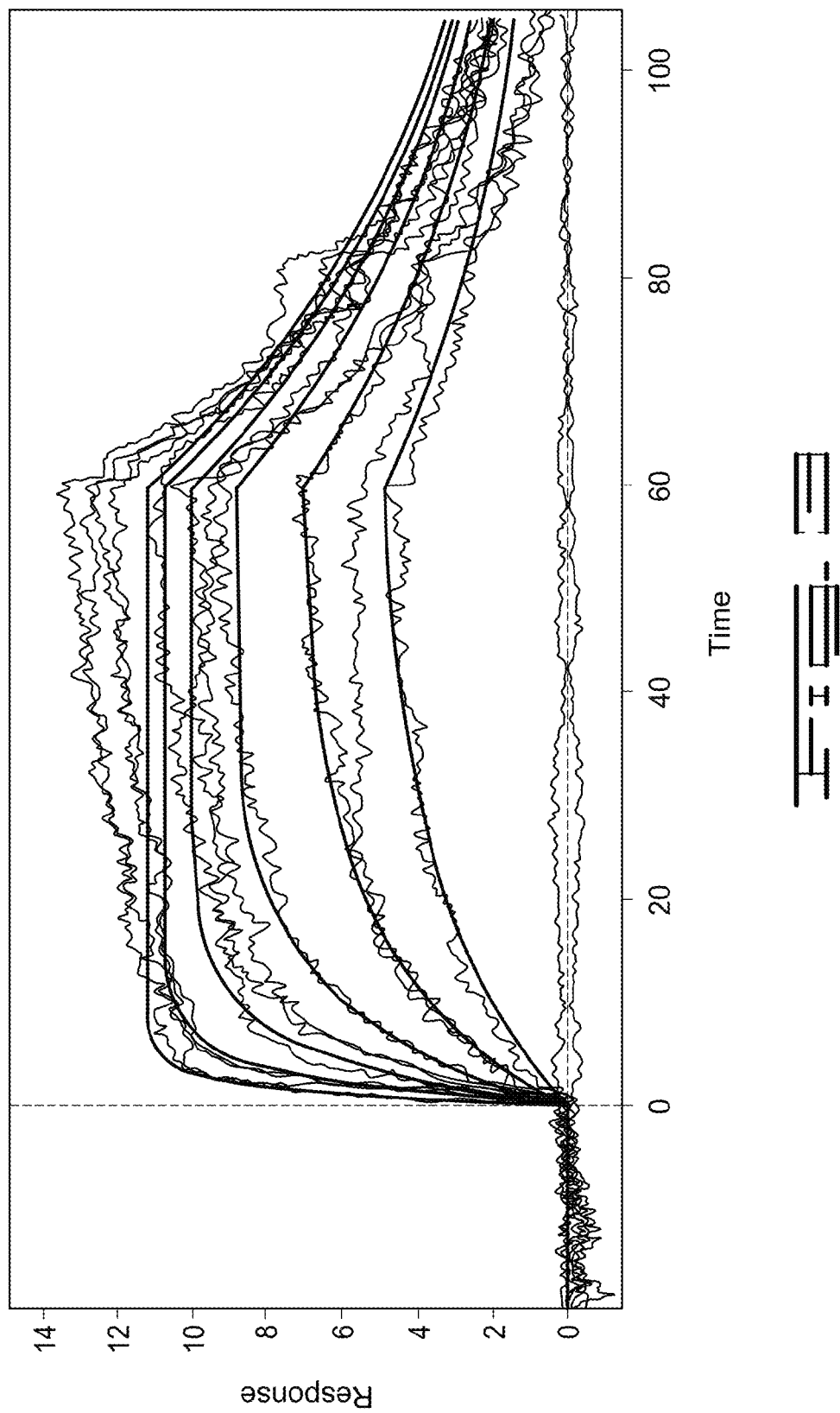
FIG. 3 provides an exemplary kinetic model fit for the binding interactions of the left panel of FIG. 2 with the reference response from the right panel of FIG. 2 subtracted.

As indicated by FIGS. 1-3, the contribution of dispersion to the raw response should be accounted for to obtain accurate results. However, the double referencing method is imperfect and the residual error is increased if the refractive index difference between the buffer and the sample is increased. The accuracy of the subtraction to correct the response depends on matching the working and reference sensing spots as closely as possible in terms of temperature, position, sensitivity, mass loading etc. In current SPR systems based on SPR imaging, it is possible to obtain response readings from any region of the plane that is being probed by the SPR such that accurate referencing should be more convenient. However, SPR imaging does not possess the sensitivity of monochromatic angle-based SPR interrogation where an elongated strip region within the flow cell is interrogated. Generally, flow cells of biosensor systems include several separate planes or sensing regions that are being actively probed by the SPR. As used herein, the term "sensing region" refers to a single region in a flow cell that is being actively probed by the surface plasmon resonance over a single range of increasing reflectance angles.

Figure 4:
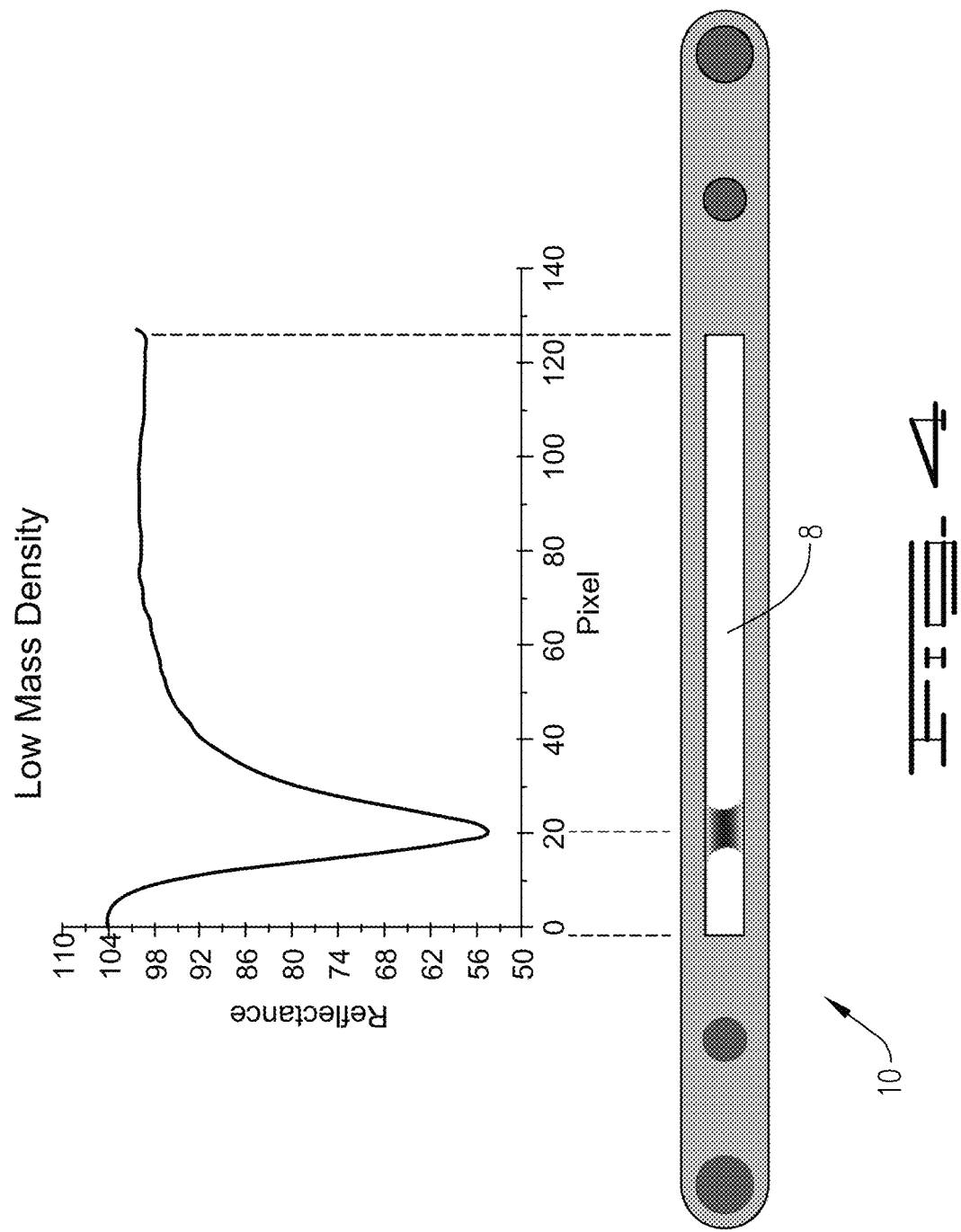
FIG. 4 depicts an exemplary low mass SPR dip mapped to a sub-region of a sensing region in a flow cell.

When nothing has been immobilized onto a surface of a sensing region, the photodiode array returns a single surface plasmon resonance dip. The pixels correlate to the SPR angles that match the resonance state when there is no additional mass loaded onto the SPR sensing surface. The resonance maps onto a particular area of sensing region 8 of flow cell 10 as in FIG. 4. It is usual to design the SPR detector to allow an SPR resonance to be measured between a refractive index of 1.333 to 1.40. When mass loading is low, the average refractive index at the sensing region will be very close to 1.334 and the SPR resonance dip will appear to one side of the photodiode array detector.

Figure 5:
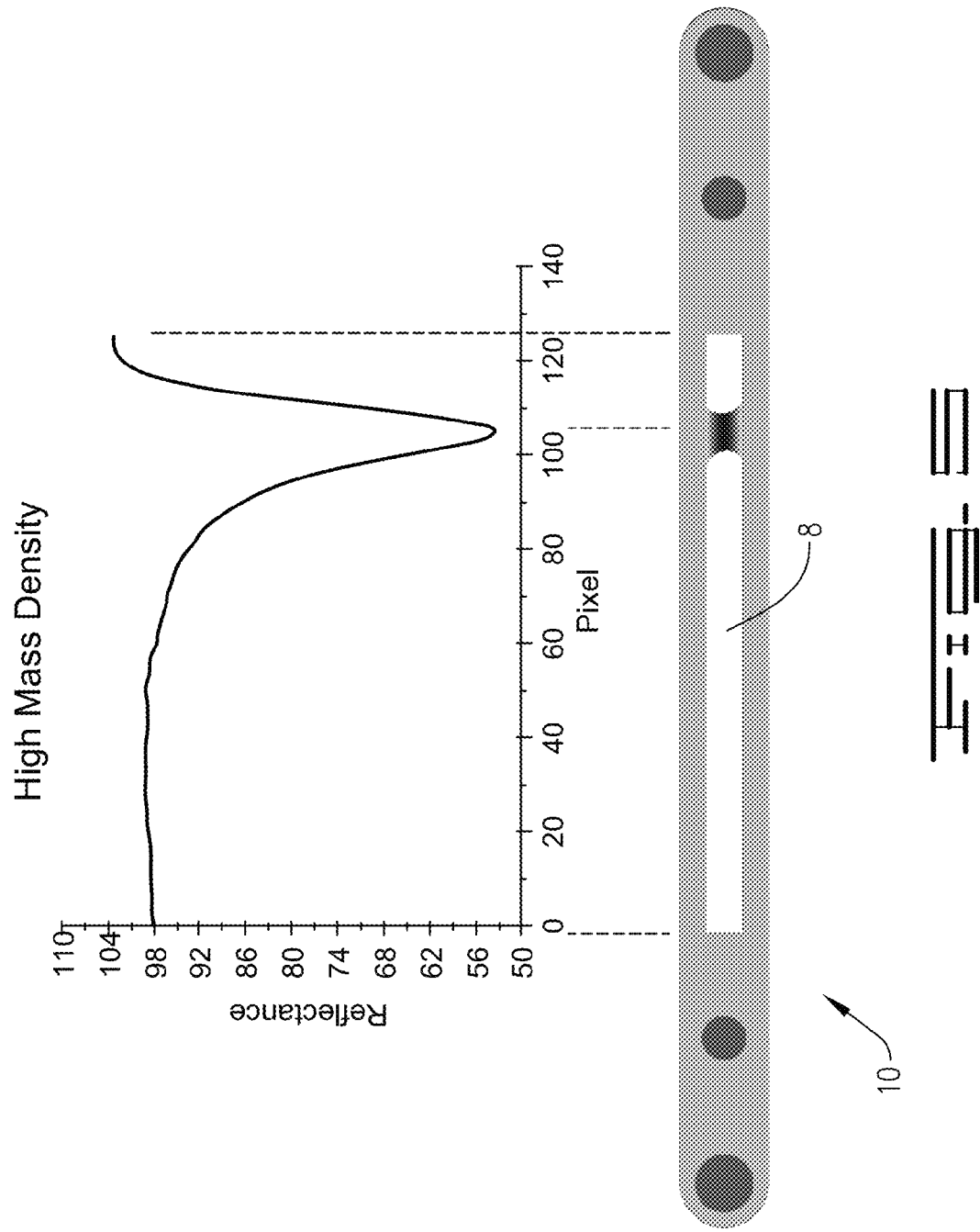
FIG. 5 depicts an exemplary high mass SPR dip mapped to a sub-region of a sensing region in a flow cell.

When a large amount of mass has been loaded onto the surface, the photodiode array returns a single surface plasmon resonance dip shifted to different SPR angles that map onto a region of the flow cell that is far from the original position before mass was loaded. The SPR dip has shifted to the right due to possessing a higher average refractive index resulting from mass loading as shown in FIG. 5.

When interrogating the SPR signal only the bottom 30% of the dip is required for computations and so the remainder of the SPR scan is not required. This type of monochromatic angle-based SPR detector is common and a single SPR dip is found per sensing region where each sensing region covers an angular range that corresponds to a refractive index measuring range of 1.333 to 1.40.

Thus, if the SPR resonance obtained when no mass is loaded on the sensing region is maintained in the presence of the second SPR resonance for high mass loading, then the low mass resonance provides a suitable reference that is very closely matched to the high mass loading resonance. This is demonstrated in FIG. 6.

A common approach is to include adjacent, but separate sensing regions that are passed in series or in parallel by the liquid stream, but each sensing region would itself also cover the entire measuring range from 1.333 to 1.40. Under these circumstances, a minimum physical separation distance is unavoidable. This distance can be reduced if the sensing regions are in parallel and housed in the same flow cell. However, this would require hydrodynamic addressing of each sensing spot within the same flow and can be complicated by cross-contamination issues. One approach to address these issues is through the use of sequential sensing regions connected in a series using a serpentine channel configuration such as flow cell 11 depicted in FIG. 7.

As shown in FIG. 7, flow cell 11 consists of a serpentine channel 12 possessing three sensing regions 14. Input/output ports 16 are positioned on each side of sensing regions 14 with separate input ports 18 and output ports 20 positioned at each end of serpentine channel 12. Shaded region 22 provides the mapped location of the SPR dip. Sensing regions 14 can have a length of about 3 mm, but can be much shorter, or longer, depending on the detector design. It is important to note that the placement of ports 16, 18, 20 which allow independent fluid addressing to each sensing region 14, but they do not allow localized access to sub-regions within sensing regions 14.

Localized fluidic access to sub-regions of a given sensing region 14 would permit the low mass SPR dip to be attained in the presence of the higher mass SPR dip. This enables dispersion effects to be subtracted when a large bulk refractive index variation between samples and buffer exists, which is common in drug discovery where high concentrations of DMSO are needed for solubility and standard assay plate preparation does not allow for bulk refractive index matching. The ability to accurately reference out the bulk refractive index effects allows resolution of low binding responses even when large bulk refractive index mismatches exist between sample and running buffer.

Localized fluidic addressing can be accomplished by adding more input/output ports 16 along each sensing region 14. However, this approach complicates the fluidic control systems required and more importantly, dispersion at these new ports can interfere with ideal referencing between the two resonance dips in a single sensing region. The present methods provide a more effective solution by creating a low mass and high mass SPR dip in a single sensing region to avoid the dispersion effects.

In conventional approaches, sensing regions either display a low mass SPR dip due to the complete absence of immobilized ligand or a high mass SPR dip due to immobilized ligand at high density. However, the present method permits both a low mass SPR dip and high mass SPR dip by selectively confining the ligand to a sub-region of the sensing regions where the high mass dip would be expected, thereby permitting a low mass dip in the sub-region void of ligand. In this instance, the low mass dip is very closely matched to the high mass dip as it is separated by a very small distance and is contained in the same sensing region. Moreover, this approach does not require the presence of fluid access holes disposed between the dip regions thereby greatly reducing dispersion that might occur between these two sub-regions. Accordingly, the dispersion experienced by sample flowing over both SPR dip regions in a single sensing region will be practically identical allowing very accurate double referencing and higher resolution of low molecular weight analyte binding.

In one embodiment, ligand is prevented from being loaded onto an entire sensing region and is confined to a sub-region where high mass loading resonance (i.e., high surface plasmon resonance angles) is expected to exist thereby providing a dual resonance where one resonance can act as an almost perfect reference for the other. This can be accomplished by localized ligand immobilization within a sub-region of a given sensing region by exploiting the behavior of a laminar flow stream as described below and depicted in FIG. 8.

FIG. 8 provides a time progression of a sample flow path (shaded area) containing the desired ligand to be immobilized on a sub-region of sensing region 40 in channel 30 in a single flow cell design. Channel 30 includes first input port 32, second input port 34, first exit port 36, second exit port 38, and sensing region 40 provided between first and second input ports 32, 34. Sample containing the desired ligand (shaded area) is injected into first input port 32 where channel 30 is pre-filled with a given buffer (not shown) before commencing the injection. At the first time point T1, first exit port 36 is open thus forcing the sample to exit immediately adjacent to first input port 32. However, by adjusting the sample flow rate, the sample interface front will migrate down channel 30 towards second input port 34 as shown at time points T2, T3 and T4 thereby enabling precise control of the position of the sample interface within the flow cell. By precisely controlling the flow rate, a counterflow stream is not necessary to control the position of the interface. Thus, the interface will simply continue to migrate down channel 30 until such time as the sample flow is stopped at a pre-calculated target position. Channel 30 is then purged with sample free buffer entering from second input port 34 and exiting at first exit port 36. In a symmetrical system, it is possible to execute this same positional control (also referred to herein as "sub-addressing") from the opposite side or even for multiple sensing regions connected in series as in the serpentine flow cell shown in FIG. 7. Additionally, a flow cell suitable for use with the present inventive method is described in U.S. Pat. No. 8,298,496, which is incorporated herein by reference.

The sub-addressing procedure described above in connection with FIG. 8 permits selective loading of ligand to a sub-region of the sensing region thereby providing a dual resonance measurement in a single sensing region as depicted in FIG. 6.

One embodiment of the current invention is depicted in FIG. 9. In this embodiment, the first step of the present method involves injecting an activating agent (light gray shading) through first input port 32 and causing the activating agent to flow over the entire sensing region 40 to second exit port 38. The second step involves injecting a deactivation solution (darker gray shading) through first input port 32 and using the sub-addressing procedure to selectively deactivate a sub-region of sensing region 40. In performing this step, the deactivating agent should be prevented from migrating to the sub-region of the sensing region that is expected to be interrogated by high SPR angles. The third step involves injecting the desired ligand (dotted area) into the channel 30 via first input port 32 and exiting via second exit port 38. As a result, the ligand injected will only be covalently bound to the high mass loading region (i.e. area interrogated by high SPR angles) that remains activated as shown in step 4. In this case, an ethyl(dimethylaminopropyl) carbodiimide (EDC)/N-hydroxysuccinimide (NHS) mixture could be used to activate carboxyl groups available at the sensing surface and a deactivation reagent such as sodium hydroxide or ethanolamine could be employed.

It is imperative that the amount of mass loaded onto the high mass region is sufficient to generate a resonance in that region. For example a 20 pixel shift to the right of the photodiode array (represents about 16,000 RU immobilized) would cause two clear SPR resonances to appear that are well resolved and can function as described. If the immobilization falls short of the target level then an additive (e.g. sucrose, glycerol etc) can be added to the buffer to shift the resonance to the correct region by making up the refractive index deficit required to map the resonance dip to the coated region.

The present method can be exploited in a variety of different manners to yield a dual resonance sensing region. For example, the entire sensing region 40 can be first exposed to an activating agent as described above and then the sub-addressing procedure can be used to restrict ligand to a particular sub-region. Alternatively, the sub-addressing procedure can be used to expose a sub-region of the sensing region to an activating agent thereby only permitting ligand loading as to the activated sub-region.

In another embodiment, rather than forming multiple resonances by changing the mass density at sub-regions in the sensing region, it is also possible to expose each sub-region to separate flow wherein the refractive index is adjusted such that a resonance dip exists for each stream intersecting the sensing region at right angles.

In another embodiment, ligand mass loading can be supplemented by co-immobilizing other non-interacting species (e.g. ovalbumin) that can confer the required mass increase yet remain neutral and non-interfering. For example, if the ligand is a low MW peptide then even at maximum immobilization capacity it will not be possible to obtain sufficient immobilized mass. The peptide could first be prepared with a biotinylated terminal group and then conjugated to a biotin binding protein such as neutravidin and this high molecular weight complex can then be immobilized at sufficient density.

In yet another embodiment, the second low refractive index resonance region may in fact be coated with a low amount of non-specific ligand or specific ligand and function as either a reference or an additional working sensing region. The sub-region fluidic addressing procedure can be used to immobilize ligands that are confined to either high or low mass regions. In this manner, a single conventional sensing region that covers the full measuring range can be subdivided into two or more sub-regions that can each maintain an SPR resonance and each can be used as either reference or working sensing regions.

In yet another embodiment, the prism through which light undergoes total internal reflection in order to generate the SPR signal can be composed by segments of optical substrates (e.g. glass, plastic, sapphire, quartz) with different dielectric properties such that each adjacent dielectric substrate is arranged such that it will present a different SPR resonance condition at the sensing surface allowing the SPR dips to be shifted with respect to each other without changing the loaded mass or the bulk refractive index at the sensing surface. In particular an electro-optical material that can exhibit the required birefringence could be employed. An on-demand mechanical mechanism where different prism segments (or exchange entire prism) can be exchanged within the optical detector could also be used.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. A method for measuring a bulk refractive index and a biomolecular interaction in a single sensing region of a biosensing system comprising the steps of:
    injecting a sample comprising an analyte through a flow cell comprising a single sensing region, wherein a first portion of the sensing region has a ligand immobilized thereon and a second portion of the sensing region is free of immobilized ligand;
    following the injection of the sample, interrogating the entire sensing region using monochromatic light over a single range of increasing reflectance angles thereby generating two or more surface plasmon resonance dips for said single sensing region;
    measuring a first response at the first portion and a second response at the second portion as the sample flows over the sensing region; and
    subtracting the second response from the first response to determine a binding response attributed to the interaction of the analyte with the ligand.

2. The method of claim 1 wherein the ligand is immobilized to the first portion at a density sufficient to generate a high mass surface plasmon resonance dip.

3. The method of claim 1 wherein the sample further comprises an additive in an amount sufficient to shift the resonance to elicit a high mass surface plasmon resonance dip at the first portion while maintaining a low mass surface plasmon resonance dip at the second portion.

4. The method of claim 3 wherein the additive is selected from the group consisting of sucrose and glycerol.

5. The method of claim 1 wherein the first portion includes a non-interacting agent that is co-immobilized with the ligand.

6. The method of claim 5 wherein the ligand is of a low molecular weight and the non-interacting agent is ovalbumin.

* * * * *